(12) United States Patent
Hudgins et al.

(10) Patent No.: US 7,927,358 B2
(45) Date of Patent: Apr. 19, 2011

(54) SPINAL STABILIZATION DEVICE

(75) Inventors: Robert Garryl Hudgins, Burnsville, MN (US); Hugh D. Hestad, Edina, MN (US)

(73) Assignee: Zimmer Spine, Inc., Minneapolis, MN (US)

(*) Notice: Subject to any disclaimer, the term of this patent is extended or adjusted under 35 U.S.C. 154(b) by 715 days.

(21) Appl. No.: 11/369,764

(22) Filed: Mar. 7, 2006

(65) Prior Publication Data
US 2007/0213719 A1 Sep. 13, 2007

(51) Int. Cl.
*A61F 2/30* (2006.01)
(52) U.S. Cl. ......... 606/262; 606/250; 606/257; 606/261
(58) Field of Classification Search .............. 606/278, 606/262, 254, 255, 256, 257, 258, 259, 264, 606/265, 246–253, 260–261, 266–277, 279
See application file for complete search history.

(56) References Cited

U.S. PATENT DOCUMENTS

| | | | |
|---|---|---|---|
| 4,653,481 A * | 3/1987 | Howland et al. | ............. 606/261 |
| 4,743,260 A | 5/1988 | Burton | |
| 5,011,484 A | 4/1991 | Bréard | |
| 5,092,866 A | 3/1992 | Breard et al. | |
| 5,375,823 A | 12/1994 | Navas | |
| 5,387,213 A | 2/1995 | Breard et al. | |
| 5,480,442 A | 1/1996 | Bertagnoli | |
| 5,496,318 A | 3/1996 | Howland et al. | |
| 5,540,688 A | 7/1996 | Navas | |
| 5,645,599 A | 7/1997 | Samani | |
| 5,658,286 A * | 8/1997 | Sava | ............................ 606/279 |
| 5,725,582 A | 3/1998 | Bevan et al. | |
| 5,836,948 A | 11/1998 | Zucherman et al. | |
| 5,888,220 A | 3/1999 | Felt et al. | |
| 6,048,342 A | 4/2000 | Zucherman et al. | |
| 6,187,048 B1 | 2/2001 | Milner et al. | |
| 6,235,030 B1 | 5/2001 | Zucherman et al. | |
| 6,261,288 B1 * | 7/2001 | Jackson | ........................ 606/250 |
| 6,419,676 B1 | 7/2002 | Zucherman et al. | |
| 6,440,132 B1 * | 8/2002 | Jackson | ........................ 606/308 |
| 6,440,169 B1 | 8/2002 | Elberg et al. | |
| 6,451,019 B1 | 9/2002 | Zucherman et al. | |
| 6,582,433 B2 | 6/2003 | Yun | |
| 6,626,944 B1 | 9/2003 | Taylor | |

(Continued)

OTHER PUBLICATIONS

PCT/US07/63267, International Search Report, Dec. 28, 2007, 6 pgs.

(Continued)

*Primary Examiner* — Eduardo C Robert
*Assistant Examiner* — Jan Christopher Merene
(74) *Attorney, Agent, or Firm* — Seager, Tufte & Wickhem, LLC (57) ABSTRACT

An implant for stabilizing adjacent vertebrae, the implant includes a stabilizing body expandable along a longitudinal axis from a first size state to a second size state. A cavity is defined in the stabilizing body for receiving a quantity of curable filler material sufficient to expand the stabilizing body from the first size state to the second size state. The implant further includes an attachment member for attaching the stabilizing body to the adjacent vertebrae. The stabilizing body is expandable along an arcuate axis to exert a restoring moment of movement on the attached vertebrae.

17 Claims, 3 Drawing Sheets

U.S. PATENT DOCUMENTS

| | | |
|---|---|---|
| 6,652,587 B2 | 11/2003 | Felt et al. |
| 7,001,431 B2 * | 2/2006 | Bao et al. .................. 623/17.12 |
| 7,655,026 B2 * | 2/2010 | Justis et al. .................. 606/259 |
| 7,744,630 B2 * | 6/2010 | Lancial ........................ 606/247 |
| 2001/0027319 A1 | 10/2001 | Ferree |
| 2001/0049531 A1 * | 12/2001 | Reiley et al. .................... 606/93 |
| 2002/0068975 A1 | 6/2002 | Teitelbaum et al. |
| 2002/0082598 A1 * | 6/2002 | Teitelbaum ..................... 606/61 |
| 2002/0133155 A1 | 9/2002 | Ferree |
| 2003/0055427 A1 * | 3/2003 | Graf ............................... 606/61 |
| 2003/0220649 A1 | 11/2003 | Bao et al. |
| 2004/0006343 A1 * | 1/2004 | Sevrain ........................... 606/61 |
| 2004/0049189 A1 * | 3/2004 | Le Couedic et al. ............ 606/61 |
| 2005/0043733 A1 | 2/2005 | Eisermann et al. |
| 2005/0165396 A1 * | 7/2005 | Fortin et al. ..................... 606/61 |
| 2005/0261682 A1 * | 11/2005 | Ferree ............................. 606/61 |
| 2007/0191845 A1 * | 8/2007 | Justis et al. ..................... 606/61 |
| 2008/0319486 A1 * | 12/2008 | Hestad et al. ................. 606/255 |

OTHER PUBLICATIONS

Medtronic News Release, "Medtronic Introduces Innovative Implant Designed to Treat Spinal Degeneration While Supporting Spinal Mobility", Sep. 29, 2003, http://www.medtronics.com/newsroom/news_20030929d.html, 2 pgs.

Spine-health.com, "The Dynesys® Spinal System clinical trial", 1999-2005, http://www.spine-heatth.com/research/trials/dynesys/dynesys01.html 5 pgs.

St. Francis Medical Technologies, Inc., "X STOP Interspinous Process Distraction for Intermittent Neurogenic Claudication", Business Briefing: Global Surgery 2003, Technology & Services, pp. 1-3.

St. Francis Medical Technologies, Inc., "St. Francis Medical Technologies Names New Chief Executive", 2004, http://www.sfmt.com/press_releases_3.asp, 2 pgs.

Zimmer, Inc., "DYNESYS® The Dynamic Stabilization System", 2005, http://www.zimmer.com, 2 pgs.

* cited by examiner

SPINAL STABILIZATION DEVICE

The present invention is related to spinal stabilization devices. More particularly, the present invention relates to devices and systems for addressing back pain originating in the vertebrae by adding devices for the flexible stabilization of the facet joints and corresponding intervertebral discs.

BACKGROUND

The spinal column is a highly complex system of bones and connective tissues that provides support for the body and protects the delicate spinal flexible connecting members and nerves of the spine. The spinal column includes a series of vertebrae stacked one on top of the other, each vertebral body including an inner or central portion of relatively weak cancellous bone and an outer portion of relatively strong cortical bone. Situated between each vertebral body is an intervertebral disc that cushions and dampens compressive forces experienced by the spinal column. A vertebral canal containing the spinal flexible connecting members and nerves is located behind the vertebral bodies.

The more than twenty vertebrae are anatomically categorized as being members of one of four classifications: cervical, thoracic, lumbar, or sacral. The cervical portion of the spine, which comprises the top of the spine up to the base of the skull, includes the first seven vertebrae. The intermediate twelve bones are the thoracic vertebrae and connect to the lower spine, which comprises the five lumbar vertebrae. The base of the spine is the sacral bone (including the coccyx). The component bones of the cervical spine are generally smaller than those of the thoracic and lumbar spine. In spite of these complexities, the spine is a highly flexible structure capable of a high degree of curvature and twist in nearly every direction. A motion segment is defined between each adjacent vertebra that may exhibit extension, flexion and twisting.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease, or trauma, such as ruptured or slipped discs, degenerative disc disease, fractured vertebra, and the like. Patients that suffer from such conditions usually experience extreme and debilitating pain as well as diminished range of motion and nerve function. These spinal pathologies may threaten the critical elements of the nervous system housed within the spinal column.

A variety of systems and surgical procedures have been disclosed in the art to alleviate the symptoms of these and other spinal pathologies. One of the most common surgical procedures today is arthrodesis, or spine fusion, of one or more spine segments. Spine fusion is used to treat many spinal disorders, including kyphosis, spondylolisthesis, and lordosis. Clinical success varies considerably, depending upon technique and indications, and consideration must be given to the concomitant risks and complications. For example, it has been shown that spine fusion decreases function by limiting the range of motion for patients in flexion, extension, rotation, and lateral bending. Furthermore, it has been shown that spine fusion creates increased stresses and, therefore, accelerated degeneration of adjacent non-fused motion segments. Also, the fusion device, whether artificial or biological, may migrate out of the fusion site.

Instead of fusing sections of the spine, various devices have been implanted into the spine to stabilize the spine without completely restricting movement. These flexible spinal stabilization methods may not result in complete spinal fusion. Some systems include implanting artificial assemblies in or on the spinal column. These assemblies may be classified as anterior, posterior, or lateral implants. As the classifications suggest, lateral and anterior assemblies are coupled to the anterior portion of the spine that is the sequence of vertebral bodies. Posterior implants generally comprise pairs of rods that are aligned along the axis of the bones and which are attached to the spinal column by hooks coupled to the lamina or to the transverse processes. Implants may also be attached by screws or attachment members inserted through the pedicles.

One posterior stabilization method includes spinal immobilization utilizing pedicle screws and rods. Other spinal systems may include a variety of other procedures and apparatuses for attending spinal problems and pain. However, there is a continual need for alternative systems and devices for stabilization of the spine.

SUMMARY

In one embodiment, the present invention is an implant for stabilizing adjacent vertebrae. The implant includes a stabilizing body expandable from a first size state to a second size state. The stabilizing body is sized and shaped to exert a restoring moment on the adjacent vertebrae upon expansion from the first size state to the second size state. A cavity is defined in the stabilizing body for receiving a quantity of curable filler material sufficient to expand the stabilizing body from the first size state to the second size state. The implant further includes an attachment member for attaching the stabilizing body to the adjacent vertebrae.

In another embodiment, the present invention is an implant for stabilizing adjacent vertebrae. The implant includes a stabilizing body expandable along an arcuate axis relative to a longitudinal axis of the spine from a first size state to a second size state. The stabilizing body is sized and shaped to exert a restoring moment on the adjacent vertebrae upon expansion from the first size state to the second size state. A cavity is defined in the stabilizing body for receiving a quantity of filler material sufficient to expand the stabilizing body from the first size state to the second size state. The implant further includes an attachment member for attaching the stabilizing body to the vertebrae.

In yet another embodiment, the present invention is a method of stabilizing a motion segment of the spine. A posterior region of adjacent vertebrae is accessed and a stabilizing body having a cavity therein is attached to the adjacent vertebrae. The stabilizing body is expanded from a first size state to a second size state by injecting a curable filler material into the cavity of the stabilizing body. A restoring moment is exerted on the adjacent vertebrae upon expansion of the stabilizing body from the first size state to the second size state. Finally, the filler material is cured.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 5 is a perspective view of an implant according to another embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The present invention includes multiple implantable devices and methods for achieving spinal stabilization. The use of the term "stabilization" in the present description refers to securing adjacent vertebrae such that the movement between them is limited to a desired amount. Stabilization may also be achieved by not only reducing movement and/or providing a restoring moment, but also by simply providing increased structural integrity between adjacent vertebrae.

The implants according to various embodiments of the present invention are adapted to exert a greater distracting force on an anterior portion of adjacent vertebrae than on a posterior portion, resulting in a restoring moment being applied in addition to stabilization. As used herein, "restoring moment" refers to a force restoring lordosis of the spine, i.e., a force restoring the normal curvature of the spine. This restoring moment will cause the posterior portion of the two vertebral bodies to move further apart (or at least reduce the amount of compressive force) at an angle relative to one another thereby providing at least a partial relief from compression of the intervertebral disk, especially on the posterior portion of the intervertebral disk.

Figure 1:
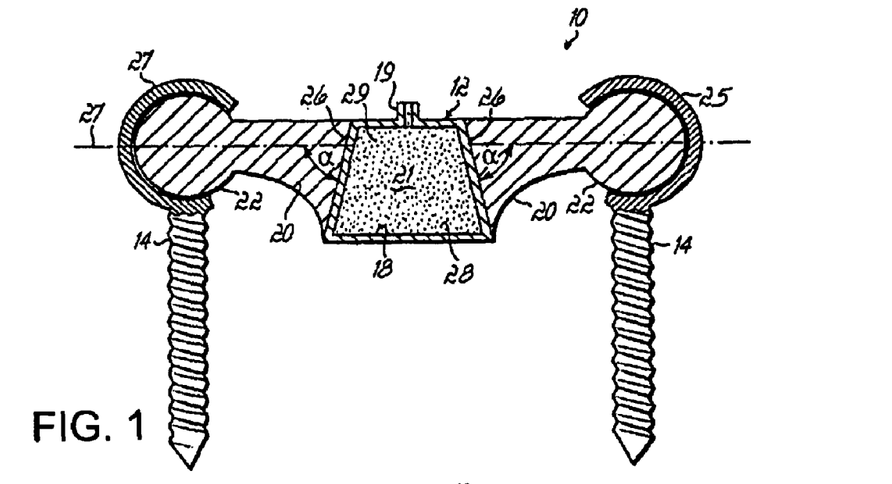
FIG. 1 shows an implant according to one embodiment of the present invention.
Figure 2A:
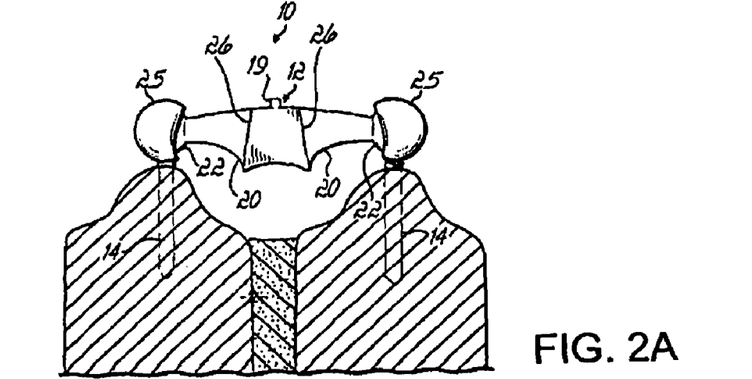
FIG. 2A is a side view of the implant of FIG. 1 attached to the vertebrae in a collapsed configuration.
Figure 2B:
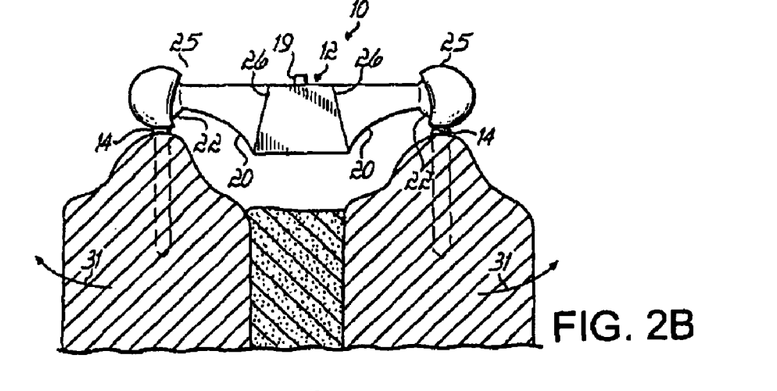
FIG. 2B is a side view of the implant of FIG. 2A in an expanded configuration.

FIG. 1 shows an implant 10 according to one embodiment of the present invention. Implant 10 may be attached to the posterior region of adjacent vertebrae, as shown in FIGS. 2A and 2B, to provide support and stabilization. The implant 10 may include a stabilizing body 12 and attachment members 14 for attaching the stabilizing body 12 to the pedicles of adjacent vertebrae.

The stabilizing body 12 includes a cavity 18 and a port 19 for accessing the cavity 18. A filler material 21 may be injected into the cavity 18 to inflate the stabilizing body 12, causing the implant 10 to expand from a first size state to a second size state. In the first size state, the implant 10 is sized for implantation according to a minimally invasive technique. Also, while in the first size state the implant 10 may be sized for attachment to adjacent vertebrae that are in a compressed state. In the second size state, the implant 10 is sized for supporting and stabilizing the vertebrae of the spine.

In general, the length of the stabilizing body 12, and thus the axis of extension upon inflation, corresponds to an axis of compression of the spine. Thus, when inflated, the implant 10 counters the spinal axis of compression, distracting the vertebrae, supporting and stabilizing the spine. As used herein, an "axis of compression" of the spine generally refers to an axis along which the vertebrae of the spine are compressed due to the effects of gravity and body weight. Although the axis of compression of the spine is generally vertical, it may vary slightly according to the natural curvature of the spine.

In one embodiment, the stabilizing body 12 is supported by a pair of pedestals 20. An interface 26 between the pedestals 20 and the stabilizing body 12, including the cavity 18, may extend at an angle $\alpha$ relative to a longitudinal axis 27 of the implant 10. The stabilizing body 12 may be cut at an angle to form the angle $\alpha$ of the interface 26. Alternately, the stabilizing body 12 may be pre-formed with a curvature. For example, a textile-type stabilizing body 12 may be woven, knit or braided over a curved mandrel to impart a preformed curvature.

In one embodiment, as illustrated in FIGS. 1-2B, the interface 26 may extend at an oblique angle relative to the axis of compression of the spine (i.e., the longitudinal axis of the stabilizing body 12). Because the interface 26 is angled relative to the axis 27 of the implant 10, an anterior portion 28 of the cavity 21 expands along the longitudinal axis 27 of the stabilizing body 12 to a greater degree than does a posterior portion 29 of the cavity 21. Expansion and extension of the implant 10 causes the implant 10 to bend slightly as the stabilizing body 12 is inflated to the second size state along a slightly arcuate axis. As the implant 10 bends, the implant 10 generates a restoring moment of movement on the motion segment of the attached vertebrae. FIG. 2B illustrates the restoring moment of movement for one embodiment of the invention as arrows 31. The angle $\alpha$ of the interface 26 may be chosen to control the restoring moment of movement 31 provided by the implant 10. The degree and direction of this moment of movement 31 may be chosen to correct abnormalities of the spine or to provide an improved or restored alignment of the vertebrae.

In one embodiment, the angle $\alpha$ of the interface 26 is chosen to restore and maintain the normal lordosis of the spine. In one embodiment, the angle $\alpha$ of the interface 26 is from about 10° to about 90° relative to a longitudinal axis of the stabilizing body 12.

In another embodiment, the angle $\alpha$ may be substantially perpendicular to an axis of compression of the spine, causing the implant 10 to expand along the axis of the spine without substantially bending (Not shown). However, a restoring moment of movement is still exerted on the attached vertebrae because a distracting force is exerted on the posterior region of the vertebrae but not the anterior region.

The stabilizing body 12 may be formed of any structure or means that acts as a pressure vessel and that is expandable primarily along a longitudinal axis. In one embodiment, the stabilizing body 12 is a braided, woven or textile tube having its fibers oriented more closely to a "hoop" direction of the tube versus a long axis of the tube.

In other embodiments, the stabilizing body 12 may be a tube-shaped balloon constructed and arranged so that its molecular structure has a preferred orientation along the hoop direction and is more compliant along its length. Thus, the balloon stretches mostly along its length and very little in a radial direction.

Expansion of the implant 10 may also be controlled by providing the stabilizing body 12 with regions that are shape-restricted or non-compliant in comparison to other portions of the stabilizing body 12. Expansion can thus be directed along a longitudinal axis and prevented in a radial direction.

The stabilizing body 12 may be made of a variety of materials that are adapted to permit expansion. In one embodiment, the stabilizing body 12 has a fabric construction. Such a fabric construction includes weaves, braids and knits, including three dimensional weaves such as honeycomb-type weaves. The fabric of the stabilizing body 12 may be constructed to permit expansion along a longitudinal axis while preventing radial expansion. Suitable materials for a fabric construction include fibers made of polyesters, polyaramids, ultra-high molecular weight polyethylenes, polypropylenes, Kevlar®, Inspectra®, Dyneema®, Vectran® and high-performance low weight highly inert materials.

In other embodiments, the stabilizing body 12 may have a bellows-type construction or otherwise include features such as folding or regions of overlap to permit expansion or to permit expansion in desired planes or axes. In still other embodiments, the stabilizing body 12 may be formed of an expandable material or have a balloon-like construction to permit expansion when subjected to internal pressurization. Such a balloon-like construction may include regions of increased rigidity or non-compliance to restrict expansion along desired planes or axes.

In one embodiment, the stabilizing body 12 is semi-permeable and includes pores or gaps. The pores or gaps may be formed in the material of the stabilizing body 12 or may be formed of gaps or openings in the weave or braid of a textile-type stabilizing body 12 as described above. The pores or gaps may be sized such that water and small particles may pass through the stabilizing body 12 while the filler material 21 is retained inside of the cavity 18.

In one embodiment, the stabilizing body 12 includes a coating chosen to provide the stabilizing body 12 with a smoother outer surface and to reduce or control leakage of the filler material 21 from the cavity 18. The coating may be formed of elastomeric or hydrogel material or other material known in the art.

In one embodiment, as is shown in FIG. 1, the port 19 may be a sleeve-like extension woven from the wall of the stabilizing body 12. In other embodiments, the port 19 may be formed by gaps or pores in the material or weave of the stabilizing body 12. In other embodiments, the port 19 may be an aperture or other means for providing access to the cavity 18.

In still other embodiments, the stabilizing body 12 may be formed of a healing or self-sealing material. Thus, the stabilizing body 12 need not include a port or aperture to the cavity 18. Instead, the filler material 21 may be injected directly through a wall of the stabilizing body 12, using, for example, a needle or syringe.

The filler material 21 may be formed of a variety of materials. In one embodiment, the filler material 21 may be an in situ curable polymer. Exemplary in situ curable polymers include bone cement, polyurethanes or other in situ curable elastomers or polymers. The filler material 21 may be adapted to facilitate or encourage bone growth. However, the filler material 21 may be formed of any hardenable or curable material that may be injected into the cavity 18 and hardened or cured to a semi-rigid or rigid state capable of supporting the vertebrae in a spaced relationship. The filler material 21 may be chosen to be self-hardening or self-curable, or hardenable or curable upon the application of heat, light, air, a curing agent or other hardening or curing means. The filler material 21 may be chosen to harden or cure shortly after injection into the cavity 18 or over a period of hours or days.

The pedestals 20 may be made of any material having suitable stiffness and wear properties. For example, the pedestals 20 may be made of a thermoplastic engineering polymer, such as polyetheretherketone (PEEK), engineering elastomer, stainless steel or titanium. In other embodiments, however, the stabilizing body 12 lacks the pedestals 20.

In one embodiment, the stabilizing body 12 lacks the pedestals 20. The cavity 18 may thus extend throughout substantially the entire stabilizing body 12. Distraction and displacement of the spine as the implant 10 expands may be controlled by the shape of the stabilizing body 12 and any regions of shape-restriction or non-compliance. In other words, a region of non-compliance, shape restriction or other substantially non-expanding structure may function as an interface means directing extension of the implant 10.

Attachment members 14 may be any type of appropriate biomedical attachment member 14 or may be replaced with any type of bone attachment anchors, screws, bone fasteners, bone attachment means, or any other fixation means for attaching the stabilizing body 12 to the spine in the desired position. When the attachment member 14 is a screw, for example, the screw type and length may be selected depending on the screw's insertion point. Moreover, the angle of insertion of the attachment members 14 may be selected to accommodate the desired attachment member 14. In still further embodiments, the stabilizing body 12 may be fixed to the bone surface using a biomedical adhesive in addition to, or in alternative to, attachment members 14. Other fixation means may include a post cemented into a cavity created in the bone. Such an implant may be similar to a dental post or a hip stem.

The pedestals 20 and the attachment members 14 may cooperate to attach the stabilizing body 12 to the vertebrae. In the present embodiment, the pedestals 20 terminate in a ball-shaped end 22 and the attachment members 14 include a complementary socket 25 to form a ball and socket joint. In other embodiments, the configuration of the ball and socket joint is reversed such that the attachment members 14 include a ball-shaped end and the pedestals 20 terminate in a complementary socket. In still other embodiments, the stabilizing body 12 and the attachment members 14 may form a hinged engagement, a snap-fit engagement or any other type of engagement means, with or without the pedestals 20.

As the implant 10 expands the ball-ends 22 of the pedestals 20 pivot within the sockets 25 of the attachment members 14. As the pedestals 20 pivot, the pedestals 20 encounter the pedicle screw sockets 25, limiting further pivoting travel. As more filler material 21 is injected into the cavity 16 to pressurize the stabilizing body 12, the implant 10 continues to inflate and lengthen. The pedestals 20 are displaced relative to one another, distracting the vertebrae and causing the implant 10 to become a load-bearing member.

In one embodiment, the ball and socket joint as shown in FIG. 1 is replaced with a rigid joint. In this embodiment, the pedestals 20 may not rotate during the initial inflation phase. Rather, the pedestals 20 may begin to displace relative to one another earlier in the inflation process. Thus, a rigid attachment of the stabilizing body 12 to the vertebrae may be employed to increase the restoring moment by making the implant 10 begin to distract the spine instead of using some of the distraction capability to permit the travel of the ball and socket joint. Also, a rigid connection may help control the spine in extension movements instead of the attachment members 14 simply rotating around the ball-end 22 of the pedestals 20.

In one embodiment of a method of positioning the implant 10 in the spine, the posterior region of the spine is first accessed according to known surgical techniques. The spine may be accessed, for example, through a minimally invasive surgical technique. The attachment members 14 may be driven into the pedicles of adjacent vertebrae and the implant 10 is installed on the attachment members 14. In one embodiment, as is shown in FIG. 2A, the ball-shaped ends 22 of the pedestals 20 may be installed in the sockets of the attachment members 14.

Once the implant 10 is attached to the vertebrae, an injection tool for injecting the filler material 21 may be brought to the implant 10 and inserted into the cavity 18 through the port 19. A sufficient amount of filler material 21 may then be injected into the cavity 18 to inflate the stabilizing body 12 and expand the implant 10 from the first size state, as is shown in FIG. 2A, to the second size state, as is shown in FIG. 2B.

When a sufficient quantity of filler material 21 has been injected into the cavity 18, the injection tool may be withdrawn, and, if necessary, the port 19 is sealed. The filler material 21 is hardened or cured to a more rigid state, supporting and distracting the vertebrae. This may involve an additional step of applying a hardening or curing agent.

The second size state may correspond to a maximum or final expansion permitted by the stabilizing body 12. Alternately, the second size state may correspond to a size state less than a maximum or final expanded size. Furthermore, the implant 10 may be expanded or inflated to an intermediate size state between the first and second size states as deemed by the user to provide a desired amount of support and distraction to the attached vertebrae and restoring moment of movement to the motion segment of the attached vertebrae. Once the filler material 21 has hardened or cured, the implant 10 may function as a load bearing member and may serve to retain the vertebrae in a spaced relationship to one another, as well as to support and stabilize the adjacent vertebrae.

Figure 3:
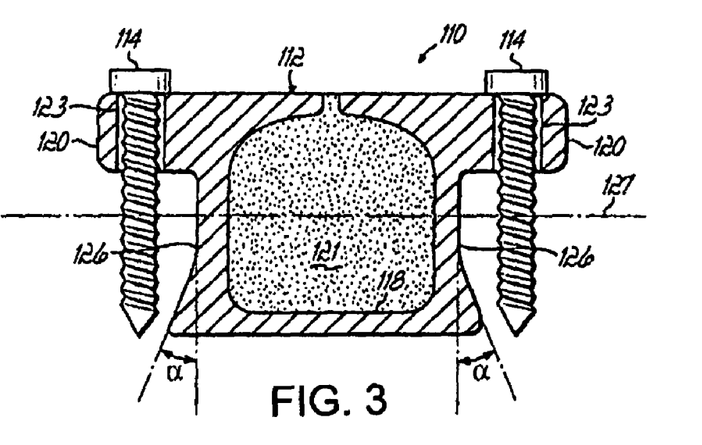
FIG. 3 is a cross-sectional view of an implant according to another embodiment of the present invention.

FIG. 3 shows an implant 110 according to another embodiment of the present invention. The implant 110 may include a stabilizing body 112 and attachment members 114 for attaching the stabilizing body 112 to the pedicles of adjacent vertebrae.

Figure 4A:
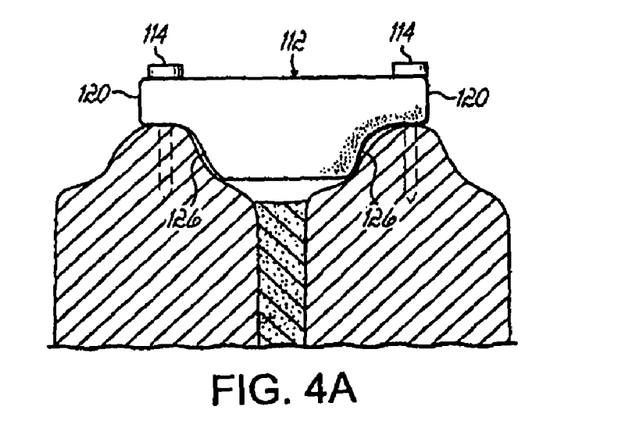
FIG. 4A is a side view of the implant of FIG. 3 attached to the vertebrae in a collapsed configuration.
Figure 4B:
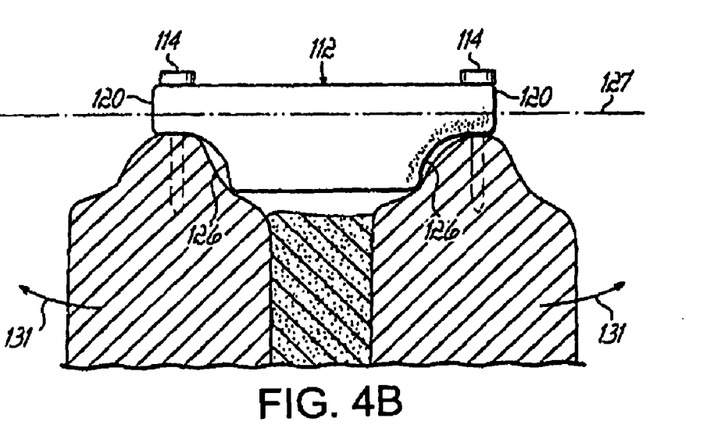
FIG. 4B is a side view of the implant of FIG. 4A in an expanded configuration.

The stabilizing body 112 includes a cavity 118 for receiving a filler material 121. Upon placement of the filler material 121 into the cavity 118, the implant 110 is expandable or inflatable from a first size state, as shown in FIG. 4A, to a second size state, as shown in FIG. 4B. In the first size state, the implant 110 may be sized for implantation into the body according to minimally invasive techniques. In the second size state, the implant 110 may be sized for supporting and stabilizing the vertebrae of the spine. The stabilizing body 112 may include a port or other means for injecting the filler material 121 into the cavity 118 as previously described. In addition, the stabilizing body 112 and filler material 121 may be made of any of the materials as previously described.

The stabilizing body 112 may be sized and shaped to be positioned in between the pedicles of adjacent vertebrae and to capture or cradle the pedicles when expanded to the second size state. The stabilizing body 112 may include slight recesses or profiling sized and shaped to conform to the shape of the pedicles.

The stabilizing body 112 may include opposing interfacing surfaces 126 extending at an angle $\alpha$ relative to a longitudinal axis 127 of the implant 110. The angle $\alpha$ of the interfacing surfaces 126 may be chosen to impart moments of movement to the spine upon expansion of the implant 110 to the second size state. For example, the angle $\alpha$ may be substantially perpendicular to an axis of compression of the spine, causing the implant 110 to expand along the axis of compression of the spine.

If, however, the interfacing surfaces 126 extend at an oblique angle relative to the axis of compression (i.e., the longitudinal axis 127 of the stabilizing body 112), expansion and extension of the implant 110 will tend to cause the implant 110 to bend slightly as the stabilizing body 112 is inflated such that the interfacing surface 126 move along an arcuate axis relative to one another. As the implant 110 bends, the implant 110 may generate a restoring moment of movement 131 on the spine which may be chosen to correct abnormalities of the spine or to provide an improved or restored alignment of the vertebrae.

The angle $\alpha$ of the interfacing surface 126 may be chosen to control the restoring moment of movement 131 provided by the implant 110. In one embodiment, the angle of the interfacing surface 126 may be chosen to restore and maintain the normal lordosis of the spine. In one embodiment, the angle $\alpha$ of the interfacing surface 126 may be from about 10° to about 90° relative to a longitudinal axis of the stabilizing body 112.

The stabilizing body 112 may be supported by a pair of pedestals 120. In the present embodiment, the pedestals 120 are tabs or wings with through-holes 123 for receiving the attachment members 114. The pedestals 120 may be rigid or flexible, and may be straight or curved. If the pedestals 120 are flexible, some of the restoring moment of movement, i.e., distracting capability, of the implant 110 may be consumed by the bending of the pedestals 120 as the implant 110 inflates. If, however, the pedestals 120 are rigid, the restoring moment of movement may be increased as previously described.

In one embodiment of positioning the implant 110 in the spine, the posterior region of the spine is first accessed according to known surgical techniques. The spine may be accessed through a minimally invasive surgical technique. The attachment members 114 are driven into the pedicles of adjacent vertebrae and the implant 110 is installed on the attachment members 114.

Once the implant 110 may be attached to the vertebrae, an injection tool for injecting the filler material 121 may be brought to the implant 110 and inserted into the cavity 118. A sufficient amount of filler material 121 may then be injected into the cavity 118 to inflate the stabilizing body 112 and expand the implant 110 from the first size state, as shown in FIG. 4A, to the second size state, as shown in FIG. 4B.

When a sufficient quantity of filler material 121 has been injected into the cavity 118, the injection tool is withdrawn, and, if necessary, a port or other access means to the cavity 118 may be sealed. The filler material 121 may be hardened or cured to a more rigid state, supporting and distracting the vertebrae. This may involve an additional step of applying a hardening or curing agent.

The second size state may correspond to a maximum or final expansion permitted by the stabilizing body. Alternately, the second size state may correspond to a size state less than a maximum or final expanded size. Furthermore, the implant 110 may be expanded or inflated to an intermediate size state between the first and second size states as deemed by the surgeon to provide a desired amount of support and distraction to the attached vertebrae and/or a restoring moment of movement to the motion segment of the attached vertebrae. Once the filler material 121 has hardened or cured, the implant 110 may function as a load bearing member and may serve to retain the vertebrae in a spaced relationship to one another, as well as to support and stabilize the adjacent vertebrae.

Figures 5A, 5B:
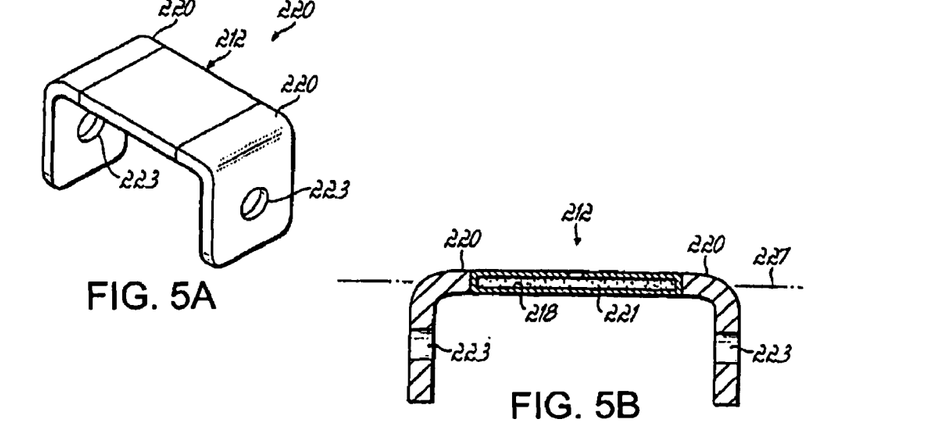
FIG. 5B is a cross-sectional view of the implant of FIG. 5A.

FIGS. 5A and 5B show an implant 210 according to another embodiment of the present invention. The implant 210 may include a stabilizing body 212 and a pair of attachment members 214 for attaching the stabilizing body 212 to the spine.

The stabilizing body 212 may have a thin, rectangular cross-sectional shape and may be curved, as shown in FIG. 5, or generally straight. The stabilizing body 212 may include a cavity 218 for receiving a filler material 221. Upon the placement of the filler material 221 into the cavity 218, the implant 210 may be expanded along a longitudinal axis 227 of the stabilizing body 212 from a first size state to a second size state. The stabilizing body 212 may include a port or other means for injecting the filler material 221 into the cavity 218 as previously described. In addition, the stabilizing body 212 and filler material 221 may be made of any of the materials as previously described.

Figure 6A:
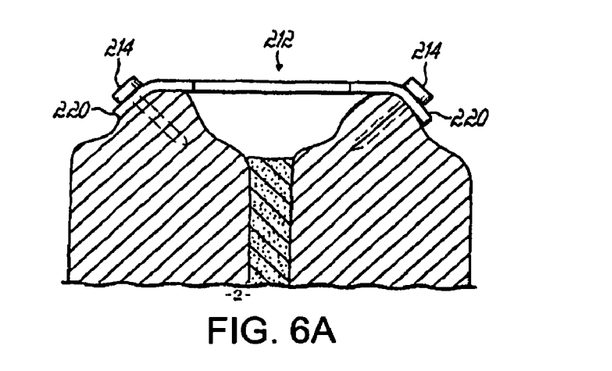
FIG. 6A is a side view of the implant of FIG. 5A attached to the vertebrae in a collapsed configuration.
Figure 6B:
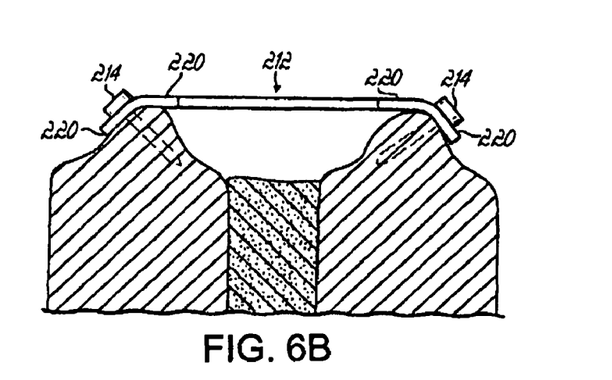
FIG. 6B is a side view of the implant of FIG. 6A in an expanded configuration.

The stabilizing body 212 may be supported by a pair of pedestals 220. The pedestals 220 may have a thin, rectangular cross-sectional shape similar to that of the stabilizing body 212. The pedestals 220 may be straight, as shown in FIG. 5A, or curved. The pedestals 220 may have through-holes 223 for receiving the attachment members 214. In one embodiment, the pedestals 220 are arranged at a perpendicular angle to a longitudinal axis of the stabilizing body 212. In this manner, one of the pedestals 220 may engage a superior surface of the superior pedicle and the other pedestal 220 may engage an inferior surface of the inferior pedicle, as shown in FIGS. 6A and 6B.

In one embodiment of positioning the implant 210 in the spine, the posterior region of the spine is first accessed according to known surgical techniques. The spine may be accessed through a minimally invasive surgical technique. The attachment members 214 are driven into the pedicles of adjacent vertebrae and the implant 210 is installed on the attachment members 214. As is shown in FIGS. 6A and 6B, the stabilizing body 210 may be attached to the pedicles without entering a space between the pedicles.

Once the implant 210 is attached to the vertebrae, an injection tool for injecting the filler material 221 is brought to the implant 210 and inserted into the cavity 218. A sufficient amount of filler material 221 is then injected into the cavity 218 to inflate the stabilizing body 212 and expand the implant 210 from the first size state, as shown in FIG. 6A, to the second size state, as shown in FIG. 6B.

When a sufficient quantity of filler material 221 has been injected into the cavity 218, the injection tool is withdrawn, and, if necessary, a port or other access means to the cavity 118 may be sealed. The filler material 221 may be hardened or cured to a more rigid state, supporting and distracting the vertebrae. This may involve an additional step of applying a hardening or curing agent.

The second size state may correspond to a maximum or final expansion permitted by the stabilizing body. Alternately, the second size state may correspond to a size state less than a maximum or final expanded size. Furthermore, the implant 210 may be expanded or inflated to an intermediate size state between the first and second size states as deemed by the surgeon to provide a desired amount of support and distraction to the attached vertebrae. Once the filler material 221 has hardened or cured, the implant 210 may function as a load bearing member and may serve to retain the vertebrae in a spaced relationship to one another, as well as to support and stabilize the adjacent vertebrae.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implant for stabilizing adjacent vertebrae separated by an intervertebral disc space, the implant comprising:
    a stabilizing body expandable from a first size state to a second size state along a generally longitudinal axis;
    a cavity defined in the stabilizing body for receiving a quantity of curable filler material sufficient to fully fill the cavity to expand the stabilizing body from the first size state to the second size state; and
    a first attachment member for attaching the stabilizing body to a posterior region of a first adjacent vertebrae and a second attachment member for attaching the stabilizing body to a posterior region of a second adjacent vertebrae such that the stabilizing body is provided in a superior-inferior orientation along the posterior regions of the adjacent vertebrae spanning and exterior of the intervertebral disc space between the adjacent vertebrae;
    wherein the stabilizing body is configured to exert a restoring moment on the first and second adjacent vertebrae by moving the first attachment member away from the second attachment member generally along the longitudinal axis during expansion from the first size state to the second size state;
    wherein the stabilizing body expands more along the longitudinal axis at an anterior portion of the stabilizing body than at a posterior portion of the stabilizing body when the cavity is fully filled with the curable filler material in the second size state.

2. The implant of claim 1 further comprising at least a first pedestal for securing the stabilizing body to one of the first and second attachment members.

3. The stabilizing body of claim 2 wherein an interface between the pedestal and the cavity extends at an angle of from about 10° to about 90° relative to the longitudinal axis of the stabilizing body from a posterior portion of the cavity to an anterior portion of the cavity.

4. The stabilizing body of claim 2 wherein the pedestal and at least one of the first and second attachment members form a ball and socket joint.

5. The implant of claim 2 wherein the pedestal is approximately perpendicular to the longitudinal axis of the stabilizing body.

6. The implant of claim 5 wherein the stabilizing body has a rectangular cross-sectional shape.

7. The stabilizing body of claim 1 wherein the stabilizing body has at least a first interfacing surface, wherein the at least first interfacing surface extends at an angle of from about 10° to about 90° relative to the longitudinal axis of the stabilizing body.

8. The implant of claim 1 wherein the stabilizing body is formed of a woven material.

9. The implant of claim 8 wherein the woven material comprises fibers substantially aligned along a horizontal plane.

10. The implant of claim 1 further comprising a port in the stabilizing body adapted for accessing the cavity.

11. The implant of claim 1 further comprising a curable filler material injectable into the cavity.

12. An implant for stabilizing first and second adjacent vertebrae separated by an intervertebral disc space, the implant comprising:
- a stabilizing body configured to be secured to a posterior region of the adjacent vertebrae such that the stabilizing body is positioned exterior of the intervertebral disc space, the stabilizing body expandable along a curvilinear path relative to a longitudinal axis of the spine from a first size state to a second size state, wherein expansion of the stabilization body is directed along the longitudinal axis and substantially prevented in a radial direction;
- a cavity defined in the stabilizing body for receiving a quantity of filler material sufficient to fully fill the cavity to expand the stabilizing body from the first size state to the second size state;
- a first attachment member for attaching the stabilizing body to the posterior region of the first vertebra; and
- a second attachment member for attaching the stabilizing body to the posterior region of the second vertebra;
- wherein the stabilizing body is configured to exert a restoring moment on the first and second adjacent vertebrae by moving the first attachment member away from the second attachment member generally along the longitudinal axis during expansion from the first size state to the second size state;
- wherein the stabilizing body is expanded along the curvilinear path when the cavity is fully filled with the curable filler material in the second size state, wherein the stabilizing body expands more along the longitudinal axis at an anterior portion of the stabilizing body than at a posterior portion of the stabilizing body when the cavity is fully filled with the curable filler material in the second size state.

13. The implant of claim 12 further comprising a first pedestal for coupling the stabilizing body to the first attachment member.

14. The implant of claim 13 wherein the first pedestal and the first attachment member form a ball and socket joint.

15. The implant of claim 13 wherein the first pedestal is fixedly couplable to the first attachment member.

16. The implant of claim 13 further comprising a second pedestal for coupling the stabilizing body to the second attachment member.

17. The implant of claim 16 wherein the first pedestal is pivotably coupled to the first attachment member by a first ball and socket joint and the second pedestal is pivotably coupled to the second attachment member by a second ball and socket joint.

\* \* \* \* \*